(12) United States Patent
Hager

(10) Patent No.: US 8,134,711 B2
(45) Date of Patent: Mar. 13, 2012

(54) DEVICE FOR REMOTE SENSING OF VEHICLE EMISSION

(76) Inventor: J. Stewart Hager, Knoxville, TN (US)

( * ) Notice: Subject to any disclaimer, the term of this patent is extended or adjusted under 35 U.S.C. 154(b) by 444 days.

(21) Appl. No.: 12/493,634

(22) Filed: Jun. 29, 2009

(65) Prior Publication Data

US 2010/0328660 A1 Dec. 30, 2010

(51) Int. Cl.
*G01N 21/47* (2006.01)
*G01N 21/00* (2006.01)
(52) U.S. Cl. ........................................ 356/446; 356/438
(58) Field of Classification Search .................. 356/446, 356/438
See application file for complete search history.

(56) References Cited

U.S. PATENT DOCUMENTS

| | | | |
|---|---|---|---|
| 4,489,239 A | 12/1984 | Grant et al. | |
| 4,924,095 A | 5/1990 | Swanson, Jr. | |
| 5,252,828 A * | 10/1993 | Kert et al. | 250/339.13 |
| 5,319,199 A | 6/1994 | Stedman et al. | |
| 5,489,777 A | 2/1996 | Stedman et al. | |
| 5,498,872 A | 3/1996 | Stedman et al. | |
| 5,637,873 A * | 6/1997 | Davis et al. | 250/339.11 |
| 5,845,639 A | 12/1998 | Hochman et al. | |
| 6,064,488 A | 5/2000 | Brand et al. | |
| 6,455,851 B1 | 9/2002 | Lord et al. | |
| 6,542,831 B1 | 4/2003 | Moosmuller et al. | |
| 7,164,132 B2 | 1/2007 | Didomenico et al. | |
| 7,375,814 B2 | 5/2008 | Reichardt et al. | |
| 7,930,931 B2 * | 4/2011 | Stedman | 73/114.71 |
| 2002/0092988 A1 | 7/2002 | Didomenico et al. | |
| 2004/0104345 A1 | 6/2004 | Kansakoski et al. | |
| 2006/0173355 A1 | 8/2006 | Alfano et al. | |
| 2006/0188869 A1 | 8/2006 | Zeskind et al. | |
| 2007/0164220 A1 | 7/2007 | Luk | |
| 2009/0238438 A1 | 9/2009 | Wardlaw et al. | |

FOREIGN PATENT DOCUMENTS

WO 2010026579 A2 3/2010

* cited by examiner

*Primary Examiner* — Roy M Punnoose
(74) *Attorney, Agent, or Firm* — Morris Manning & Martin, LLP; Tim Tingkang Xia, Esq.

(57) ABSTRACT

In one aspect, the present invention relates to a device for remote sensing of emissions of a vehicle driven on a road. In one embodiment, the device includes a source for emitting a beam of light and transmitting the emitted light through an exhaust plume emitted from the vehicle to the surface of a lane of the road on which the vehicle is driven, wherein the transmitted light is scattered at the surface of the lane; a detector for receiving at least one portion of the scattered light scattered from the surface of the lane; and a processor for processing the received light therein to provide one or more spectra of the received light so as to determine components and concentrations of the exhaust plume. The source and the detector are located in the same side of the road.

26 Claims, 9 Drawing Sheets

DEVICE FOR REMOTE SENSING OF VEHICLE EMISSION

CROSS-REFERENCE TO RELATED PATENT APPLICATION

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

FIELD OF THE INVENTION

The present invention generally relates to emission detection of vehicles, and more particularly to an apparatus that utilizes the LIDAR technology to remotely detect emission of vehicles.

BACKGROUND OF THE INVENTION

It is known that vehicle emissions are a major contributor to air pollution. To identify vehicles that are releasing excessively polluting emissions, annually vehicle emission inspection is mandated in many countries. Accordingly, various emission inspection systems have been developed for the vehicle emission inspection. Generally, these systems are very expansive, and their operations require in a vast amount of labor and skill. Additionally, they are operated in testing stations to detect emissions of vehicles in either idling or artificially loaded conditions. Although the detection provides general baseline information regarding vehicle emissions, it is not representative of "real world" driving.

Recently, remote emission sensing systems have been developed for detecting emissions of vehicles driven on the road. For example, U.S. Pat. Nos. 5,319,199 and 5,498,872 to Stedman et al. discloses a remote sensing system in which the light source 910 and detector 930 are oppositely located on both sides of the road 901, respectively, as shown in FIG. 9(a). For such an arrangement, a beam of light 915 generated from the source 910 passes through an exhaust plume 940 emitted from a vehicle 905 driven on the road 901, thereby carrying absorption signal associated with components and concentrations of the exhaust plume 940. The beam 915 is collected by the detector 930 for analyzing the components and concentrations of exhaust plume 940. Alternatively, as shown in FIG. 9(b), the light source 910 and detector 930 are located on the same side of the road 901. And two reflectors 950 located on the opposite side of the road 901 are used to reflect the beam 915 generated from the source 910 to the detector 930 with two passes through the vehicle exhaust plume 940, which increases the absorption signal.

However, for such remote emission sensing systems, the source, detector and reflectors are set up in both sides of the road, extra cares need being taken during the installation and maintenance. On the other hand, it is difficult to correctly associate each vehicle with its emission data when more than one vehicle is present in multiple lanes. For example, if multiple vehicles are present at the sensing location, each vehicle's exhaust plume may contribute emissions. Thus, the existing systems are not able to differentiate among several exhaust plumes.

Also, the accuracy can depend on the height of the beam of light going across the road. The height of the tail pipe varies from vehicle to vehicle. The emission reads will vary depending on whether the beam is at the height of the tail pipe, lower or higher where the exhaust has time to dilute before detection. By looking down on to the exhaust, the tail pipe height is immaterial.

Therefore, a heretofore unaddressed need exists in the art to address the aforementioned deficiencies and inadequacies.

SUMMARY OF THE INVENTION

In one aspect, the present invention relates to a device for remote sensing of emissions of a vehicle driven on a road. In one embodiment, the device includes a source for emitting a beam of light and transmitting the emitted light through an exhaust plume emitted from the vehicle to the surface of a lane of the road on which the vehicle is driven, wherein the transmitted light is scattered at the surface of the lane; a detector for receiving at least one portion of the scattered light scattered from the surface of the lane; and a processor for processing the received light therein to provide one or more spectra of the received light so as to determine components and concentrations of the exhaust plume. The source and the detector are located in the same side of the road.

In one embodiment, the source has a halogen light source. A collimating optics is adapted for collimating the emitted light and transmitting the collimated light through the exhaust plume to the surface of the lane. In one embodiment, the collimating optics comprises a first concave mirror and a second concave mirror positioned in relation to the source such that the first concave mirror receives the beam of light emitted from the source and reflects the received light to the second concave mirror, the second concave mirror, in turn, collimates the reflected light and transmits the collimated light through the exhaust plume to the surface of the lane. The first concave mirror and the second concave mirror define a focus therebetween, and a chopper is placed on the focus.

When the beam of light is a broadband light, one or more filters are adapted and positioned in front of the detector. Each filter has a predetermined bandwidth.

In another one embodiment, the source comprises light emitting diodes (LEDs).

In yet another one embodiment, the source comprises a laser. In one embodiment, the laser includes a diode laser. In the case, both the source and the detector are placed on the same optical axis.

The device further includes a collecting optics positioned in an optical path between the source and detector for collecting the scattered light scattered from the surface of the lane and delivering the collected light to the detector, where the collecting optics has a focus on the optical path, and the detector is placed on the focus. In one embodiment, the collecting optics comprises a Newtonian telescope. In another embodiment, the collecting optics comprises a concave mirror.

In one embodiment, the detector includes a plurality of photosensors, each photosensor generating an electrical signal responsive of the scattered light received, where the electrical signal is indicative of the absorption of the scattered light by the exhaust plume. In another embodiment, the detector comprises an array detector capable of capturing images of the exhaust plume.

In one embodiment, the processor comprises a spectrometer.

In another aspect, the present invention relates to a device for remote sensing of emissions of a vehicle driven on a road.

In one embodiment, the device includes a source for emitting a beam of light and transmitting the emitted light through an exhaust plume emitted from the vehicle to the surface of a lane of the road on which the vehicle is driven, wherein the transmitted light is scattered at the surface of the lane; a detector for receiving light and processing the received light therein to provide one or more spectra of the received light, wherein the detector and the source are located in the same side of the road and define an optical path therebetween; and a collecting optics positioned in the optical path for collecting the scattered light scattered from the surface of the lane and delivering the collected light to the detector.

The source comprises a halogen light source, LEDs, or a laser. The collecting optics comprises a concave mirror or Newtonian telescope.

In one embodiment, the detector comprises a plurality of photosensors, each photosensor generating an electrical signal responsive of the scattered light received, wherein the electrical signal is indicative of the absorption of the scattered light by the exhaust plume. The detector may further include a processor responsive to the electrical signals from the plurality of photosensors for determining components and concentrations of the exhaust plume.

In another embodiment, the detector has an array detector capable of capturing images of the exhaust plume.

In one embodiment, the device includes a license plate reader for identifying the vehicle to be detected. Further, the device may have a speed reader for detecting the speed of the vehicle so as to determine an exhaust pattern of the vehicle.

In yet another aspect, the present invention relates to a device for remote sensing of emissions of a vehicle. In one embodiment, the device includes a source for emitting a beam of light and transmitting the emitted light through an exhaust plume emitted from the vehicle to a surface at which the transmitted light is scattered, and a detector for receiving at least one portion of the scattered light scattered from the surface and processing the received light therein to provide one or more spectra of the received light so as to determine components and concentrations of the exhaust plume. The surface is corresponding to the bottom surface of a bridge through which the vehicle is driven, or the surface of a lane of a road on which the vehicle is driven.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, wherein.

DETAILED DESCRIPTION OF THE INVENTION

Figure 1:
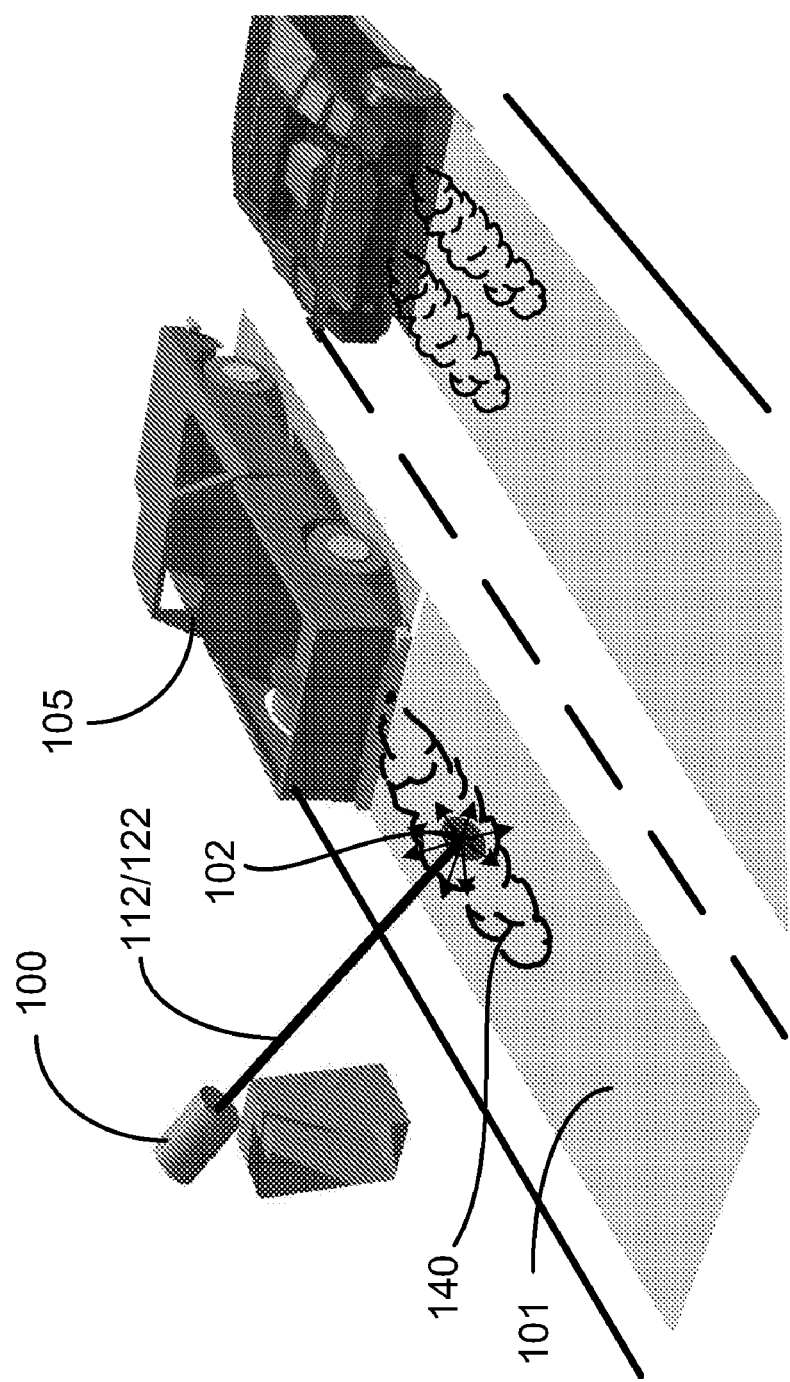
FIG. 1 shows schematically a device for remote sensing of vehicle emission according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "LIDAR" is an acronym or abbreviation of "light detection and ranging", and is an optical remote sensing technology that measures properties of scattered light to find range and/or other information of a distant target.

As used herein, the terms "comprising," "including," "having," "containing," "involving," and the like are to be understood to be open-ended, i.e., to mean including but not limited to.

The description will be made as to the embodiments of the present invention in conjunction with the accompanying drawings in FIGS. 1-8. In accordance with the purposes of this invention, as embodied and broadly described herein, this invention, in one aspect, relates to an apparatus that utilizes the LIDAR technology to detect emissions of a vehicle. The invented device is a portable roadside system for detection of exhaust emissions of a vehicle having internal combustion engines and driven on a lane of a road. While the conventional emission detection devices use mirrors or retro reflectors to return a beam of light emitted from a source and transmitted through an exhaust plume of the vehicle to a detector, the invented device uses the LIDAR technology. The beam of light emitted from a source is directed downwards, passing through the exhaust plume, toward the surface of a traffic lane of a road on which the vehicle is driven. The transmitted light is then scattered at the surface of the traffic lane. The invented device collects the scattered light from the surface of the traffic lane with concave mirrors to the detector. Further, a detector array can be utilized to acquire images of the exhaust plume and the surface of the road for determining the column concentrations of gas pollutants in the exhaust plume.

Figure 2:
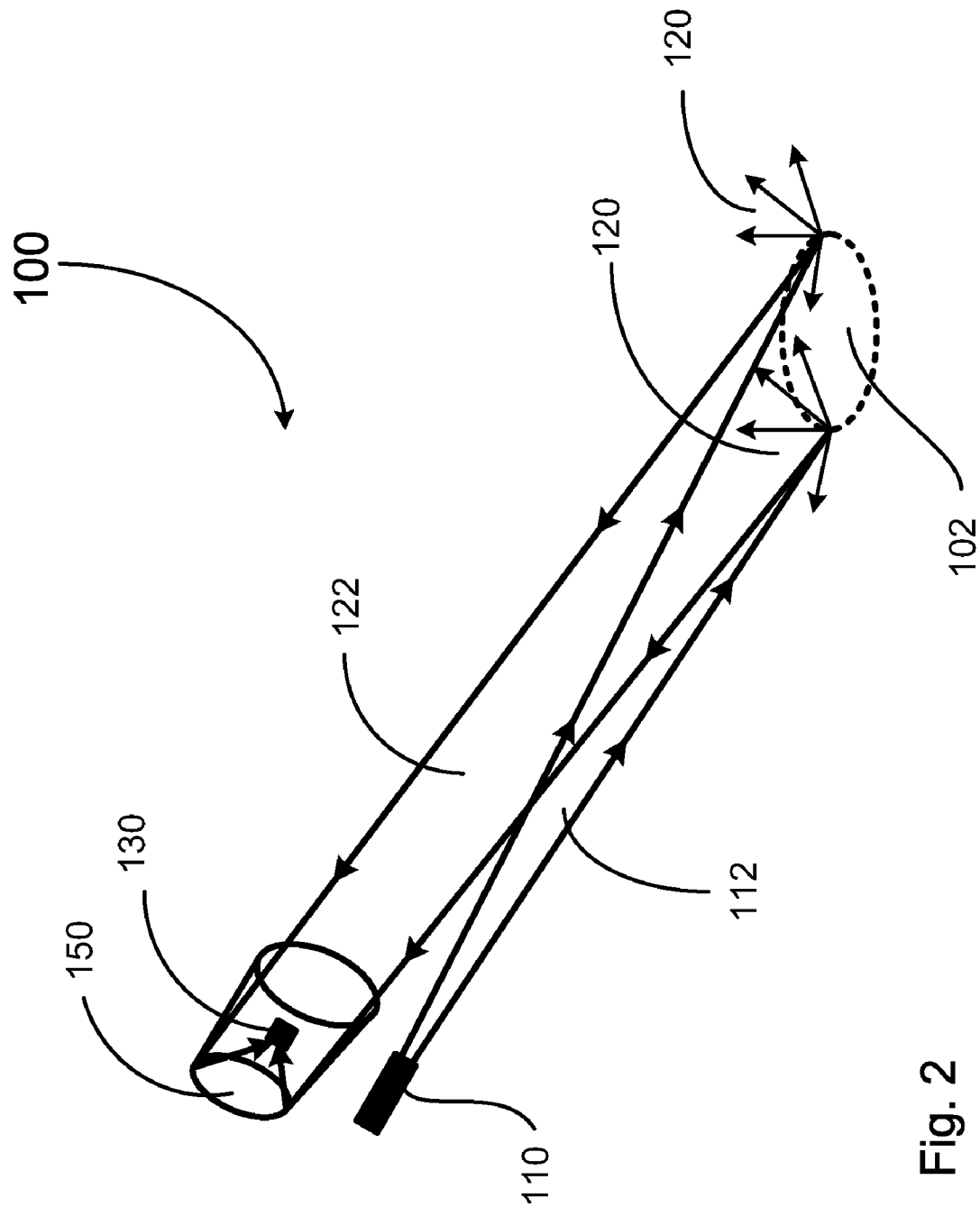
FIG. 2 shows schematically an optical diagram of the remote sensing device according to one embodiment of the present invention.

Referring to FIGS. 1 and 2, and particularly to FIG. 2, a device 100 for remote sensing of vehicle emission is shown schematically according to one embodiment of the present invention. The device 100 includes a source 110, a detector 130 and an optical collecting optics 150. The source 110 and the detector 130 define an optical path along which a beam of light travels from the source 110 to the detector 130, and the collecting optics 150 is positioned in the optical path. Further, the source 110, the detector 130 and the collecting means 150 are located in the same side of the road.

In operation, the source 110 emits a beam of light 112 that is transmitted through an exhaust plume 140 emitted from the vehicle 105 to the surface 102 of a lane 101 of the road on which the vehicle 105 is driven. The transmitted light 112 is scattered, in a $2\pi$ steradian hemisphere, at the surface 102 of the lane 101. A portion 122 of the scattered light 120 along the optical path is collected by the concave mirror (the optical collecting optics) 150. The concave mirror 150, in turn, delivers the portion 122 of the scattered light 120 to the detector 130 that is located at the focus of the concave mirror 150. The detector 130 may includes a plurality of photosensors. Each photosensor generates an electrical signal responsive of the scattered light received. The electrical signal is indicative of the absorption of the scattered light by the exhaust plume. Furthermore, the device 100 has a processor (not shown) in communication with the detector 130 to process the electrical signals from the detector 130 so as to determine components and concentrations of the exhaust plume. In one embodiment, the processor may have a spectrometer.

Additionally, the focal plane of the concave mirror 150 can be used to position several different detectors that image different sections of the road. One can image a strip of the road surface by using a parallel array detector.

Different light sources are utilized requiring different configurations and detector technologies. The light sources are pulse or chopped in accord with lock-in amplifiers to increase sensitivity and to differentiate light sources.

The light source can be directed to individual lanes of traffic and therefore can detect emissions of vehicles from specific lanes. Residual, low concentration exhausts from the neighboring lanes of traffic and be taken into account and deducted.

Also the light source can be directed to areas on the lane of traffic that would most likely target vehicles of different manufacturers that have tailpipes at different positions. Detecting the exhausts soon after it exits the tailpipe will allow detecting the highest concentrations of molecules of the exhaust before they mix with the ambient air. This will give the most precise remote sensing of the vehicle emissions. An example would be GM SUV tail pipe being positioned just after the right rear tire. Collection optics could image the right edge of the road to target the GM SUVs. A reading of the exhaust could be sensed before the rear of the vehicle passes the device, giving one a reading of the high possible concentrations.

The device can measure concentration of pollutants such as hydrocarbons, CO, $CO_2$, $SO_2$, $NH_3$ and $NO_2$ of passing vehicles. The device also has a license recognition system and a velocity radar system to characterize the emission profile of different vehicles. The license recognition system and the velocity radar system can be those available on the market. Accordingly, the invented device is much less expensive, and yet with superior performance, than the conventional devices. Additionally, a system of remote sensing of vehicle exhaust may comprises several the invented devices as disclosed above and one license recognition and velocity radar system.

Figure 8:
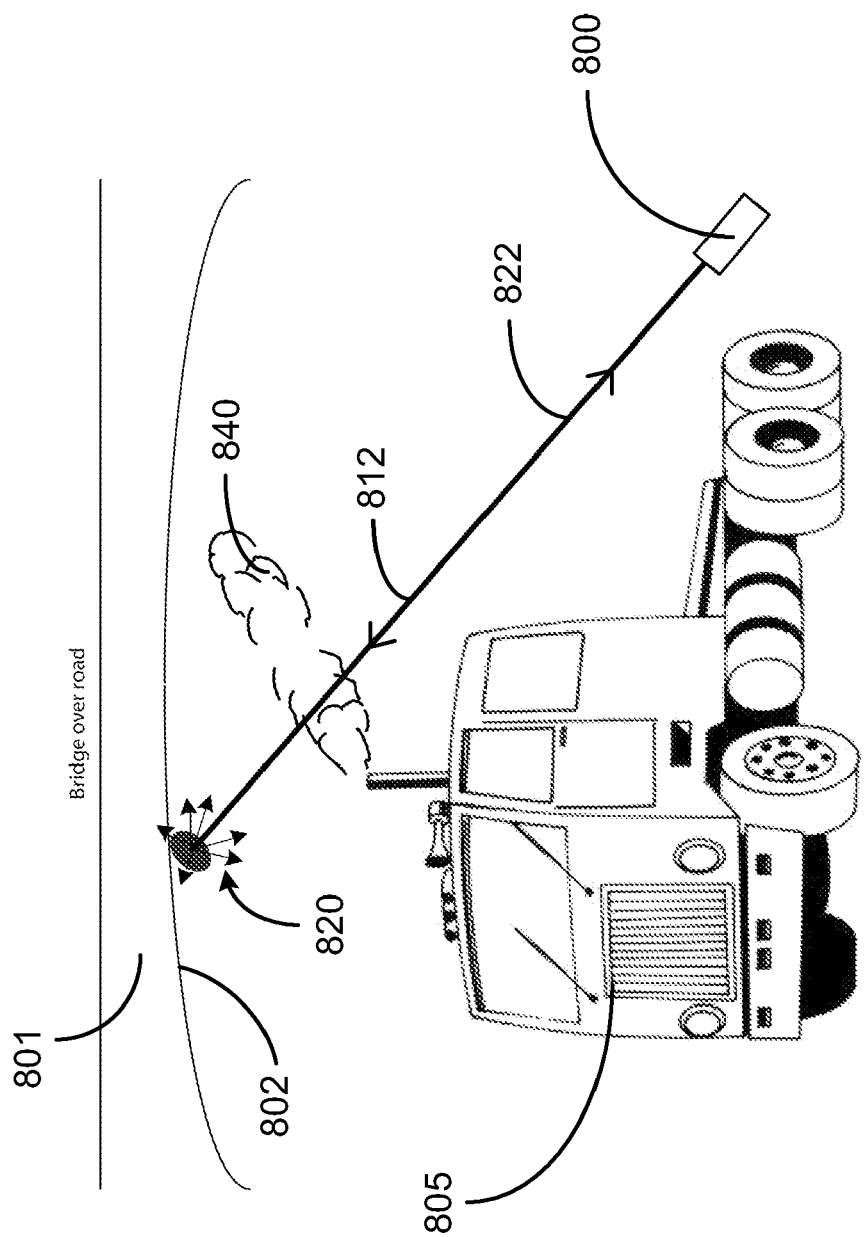
FIG. 8 shows schematically a device for remote sensing of vehicle emission according to one embodiment of the present invention.
Figure 9:
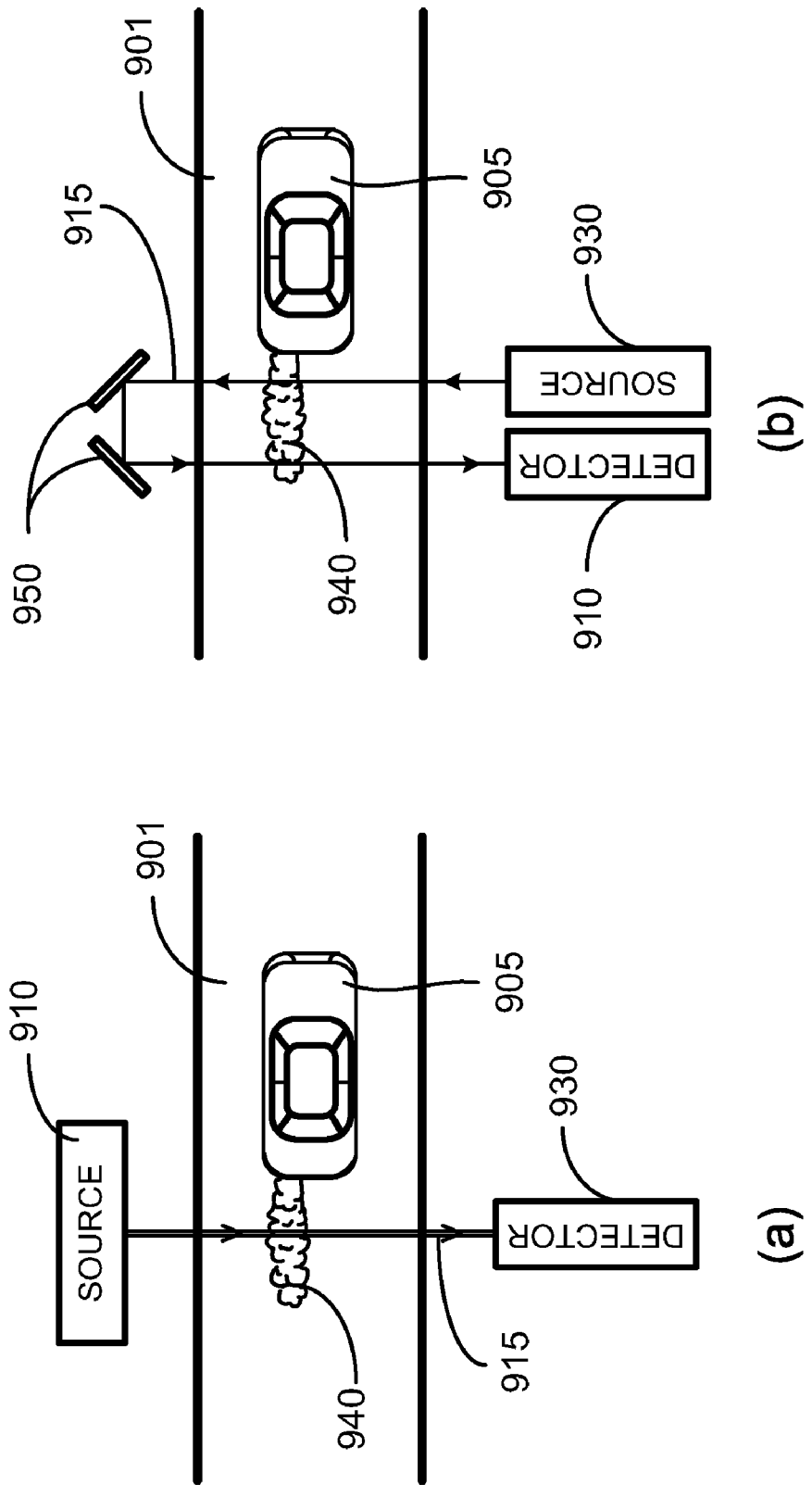
FIG. 9 shows schematically a conventional device for remote sensing of vehicle emission.

Additionally, the same device can also be used to remote sensing of emissions of a vehicle such as a heavy-duty truck that has the exhaust pile installed on its top, whereby the emitted exhaust plume is far away from the surface of the road on which the vehicle is driven. In this case, a bottom surface of bridge or the like can be utilized to scatter the beam of light that transmits through the exhaust plume. As shown in FIG. 8, the device 800 has a source and a detector, as disclosed above, which are housed inside a device case. The device 800 is set up such that the beam of light 812 emitted from the source is directed upwards at the surface 802 of a bridge 801, instead of downwards at the lane surface of the road on which the vehicle 905 is driven. The beam of light 812 is transmitted through the exhaust plume 840 emitted from the vehicle 805 towards the surface 802 of the bridge 801. The transmitted light is then scattered at the surface 802 of the bridge 801. At least one portion 822 of the scattered light 820 is received by the detector and processed therein so as to determine components and concentrations of the exhaust plume. Additionally, a processor in communication with the detector may be assembled inside the device case or outside the device case, for processing the data signals generated by the detector responsive to the scattered light.

Without intent to limit the scope of the invention, exemplary devices and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention.

Light Sources

Figure 3:
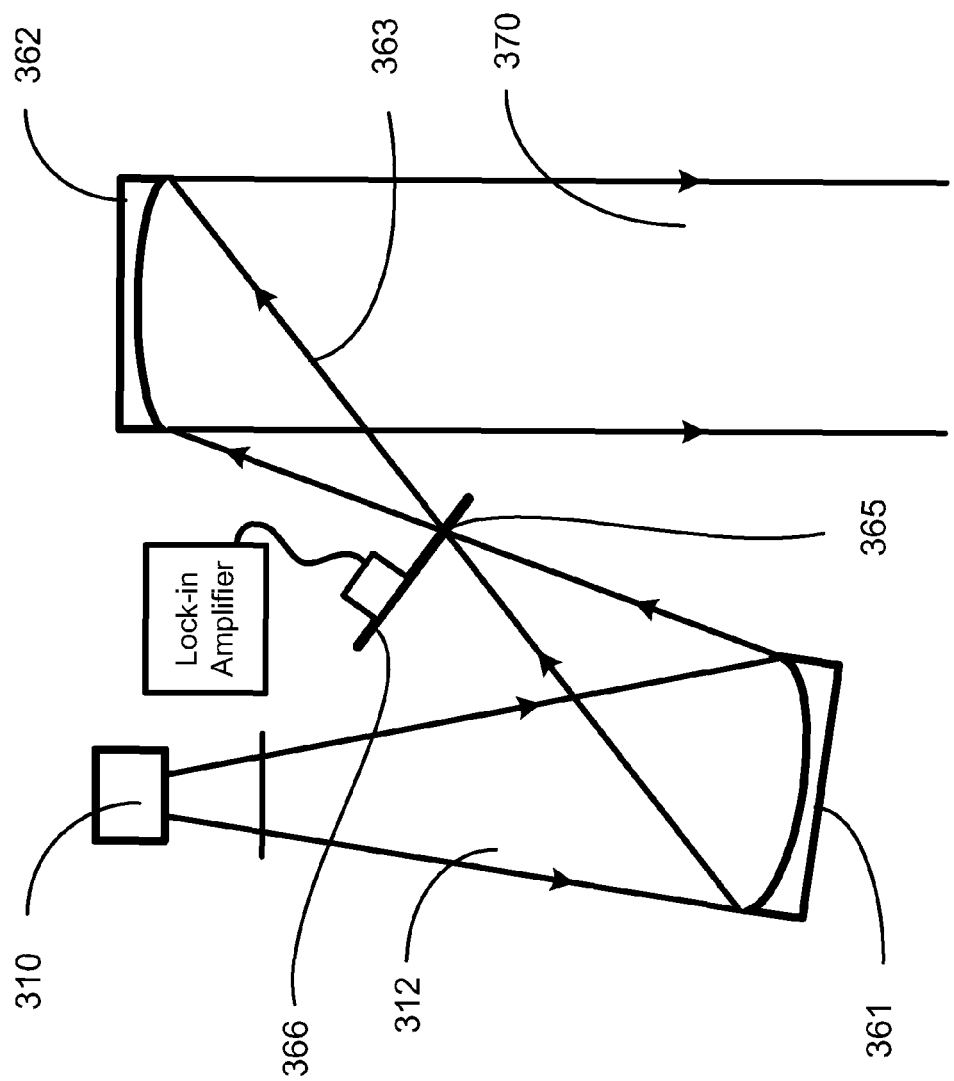
FIG. 3 shows schematically a collimating optics utilized in the remote sensing device according to one embodiment of the present invention.

A Broadband Source—Halogen Light Bulb: In one embodiment, a halogen light bulb such as a car headlight is used as the source. For such a broadband source, a collimating optics can be utilized to collimate the beam of light emitted from the halogen light bulb and to transmit the collimated light through the exhaust plume to the surface of the lane. As shown in FIG. 3, the collimating optics includes a first concave mirror 361 and a second concave mirror 362 positioned in relation to the broadband source 310 such that the first concave mirror 361 receives the beam of light 312 emitted from the source 310 and reflects the received light 312 to the second concave mirror 362. The second concave mirror 362, in turn, collimates the reflected light 363 and transmits the collimated light 370 through the exhaust plume to the surface of the lane. The first concave mirror 361 and the second concave mirror 362 define a focus 365 therebetween. At the focus 365, the reflected light 363 is chopped with a wheel or bell chopper 366. The chopper signal is fed in to a dual-phase lock-in amplifier. The lock-in amplifier then amplifies the signal without adding noise.

This broadband source radiates from ultraviolet to infrared light out to 5 μm. This covers strong fundamental absorption bands of CO and $CO_2$ as well as strong violet and ultraviolet bands of $NO_2$, NO and $SO_2$. Filters can be used to isolate specific bands of these molecules, along with water vapor, hydrocarbons, ammonia and others.

A modulated halogen light source is strong in intensity and can be scattered over the complete lane. Mirrors can be used to collect the light anywhere it is shining Depending on the focal length and distance, these mirrors can image specific illuminated positions on to a detector. This allows different paths or position to be used to target different tailpipe positions.

Light Emitting Diodes (LEDs): LEDs can be modulated and thus end the need for a physical chopper. They have also narrower bandwidth than the in the past. They have about the same bandwidth as filters. Therefore there is no need for filters on the detectors. The modulation of LEDs can be in the MHz range. This gives you more flexibility to filter out ambient noise. This noise is mainly due to thermals coming from the road surface.

Diode Lasers: The telecommunication industry as open up diode lasers to low cost. The telecommunication industry uses fiber optics and diode lasers to transmit large amounts of data, long distances. Because of the material of the fiber optics the average wavelength of these lasers is approximately 1.5 μm. There are infrared absorption bands of $CO_2$, CO, $H_2O$, $NH_2$ and others in this region. The laser diodes and InGaAs detectors are extremely inexpensive and extremely high quality because of the mass production and cost affectedness of sensitivity of the products. This allows for detection of these bands even though some are extremely weak.

Diode lasers can be used to remote sense temperature of exhaust, because of the Boltzmann factor and the extreme narrowness of a laser line. The thermal distribution of rotational levels is not simply given by the Boltzmann factor $e^{-E/kT}$. The number of molecules $N_J$ in the rotational level J of the lowest vibrational state at the temperature T is proportional to (G. Herzberg. *Spectra of Diatomic Molecules*, $2^{nd}$ ed. D. Van Nostrand Co. 1950):

$$N_J = (2J+1)e^{-BJ(J+1)hc/kT}$$

Figure 4:
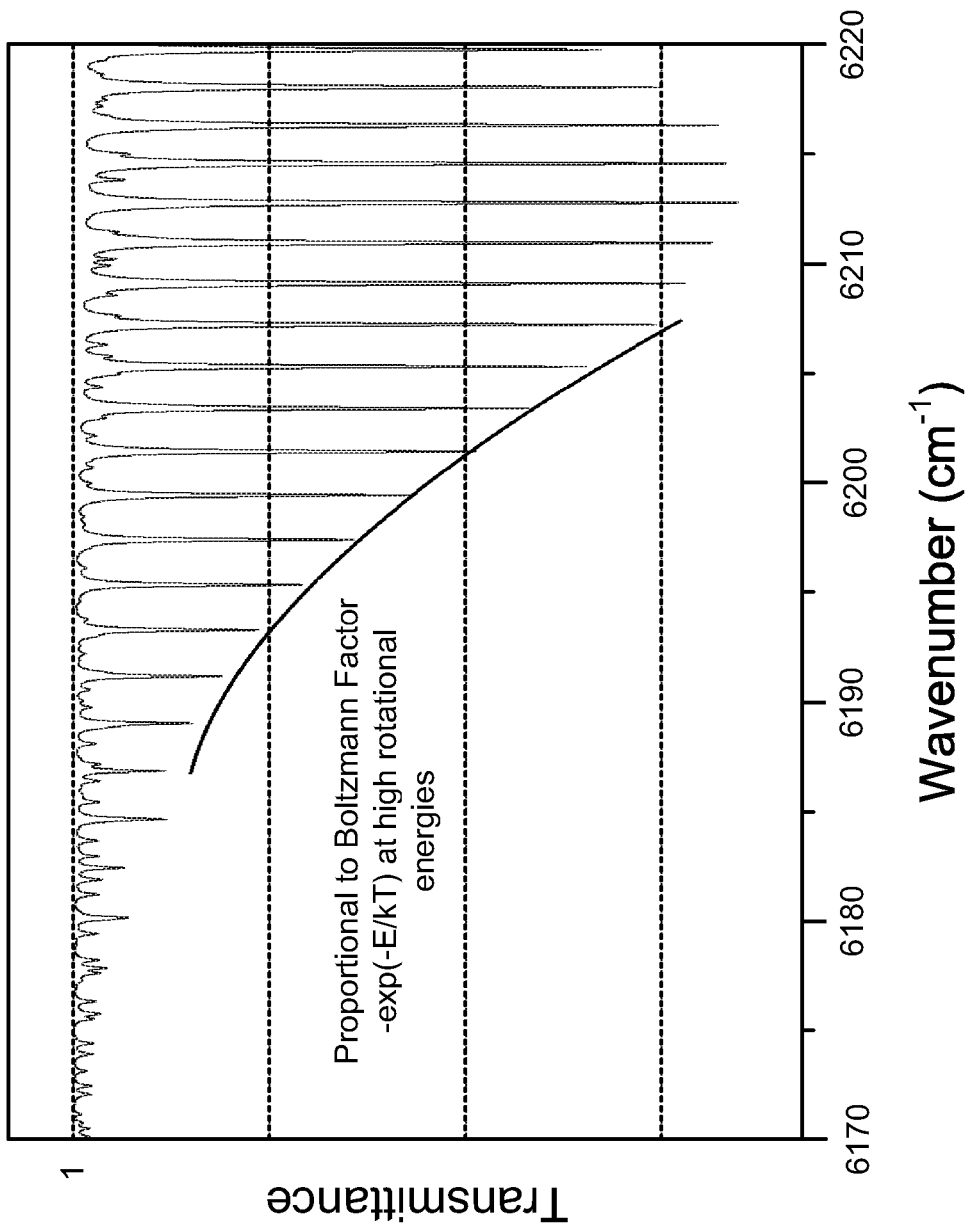
FIG. 4 shows the absorption lines at higher rotational energies follow the Boltzmann Factor.

This infers the higher the J value or rotational energy the more the exponential term dominates. One can then back out the temperature of the exhaust using this relationship. FIG. 4 shows the spectra of CO2 in the 1.5 μm region. The Boltzmann factor can be seen in the higher rotational energies. The absorption lines at higher rotational energies follow the Boltzmann Factor and therefore can be used to calculate the temperature of the exhaust.

The mixing ratio of molecules in the exhaust changes as a vehicle warms up. A cold car pollutes more than a hot one. One can detect the temperature along with the concentration of gases in an exhaust plume using two or three different wavelength lasers. One can then adjust concentration expectations due to the temperature of the engine and tailpipe.

Diode lasers have an FWHM (Full Width at Half Maximum) in the range of about 6-10 MHz. This means it can sit on top of one absorption line. Different wavelength lasers can be selected to give the slope or shape of the Boltzmann factor. Then the temperature of the exhaust can be calculated. These lasers can be modulated at different frequencies. This allows the different detectors with lock-in amplifiers to be used to differentiate between the lasers illuminating the same spot.

Detection Devices

Figure 5:
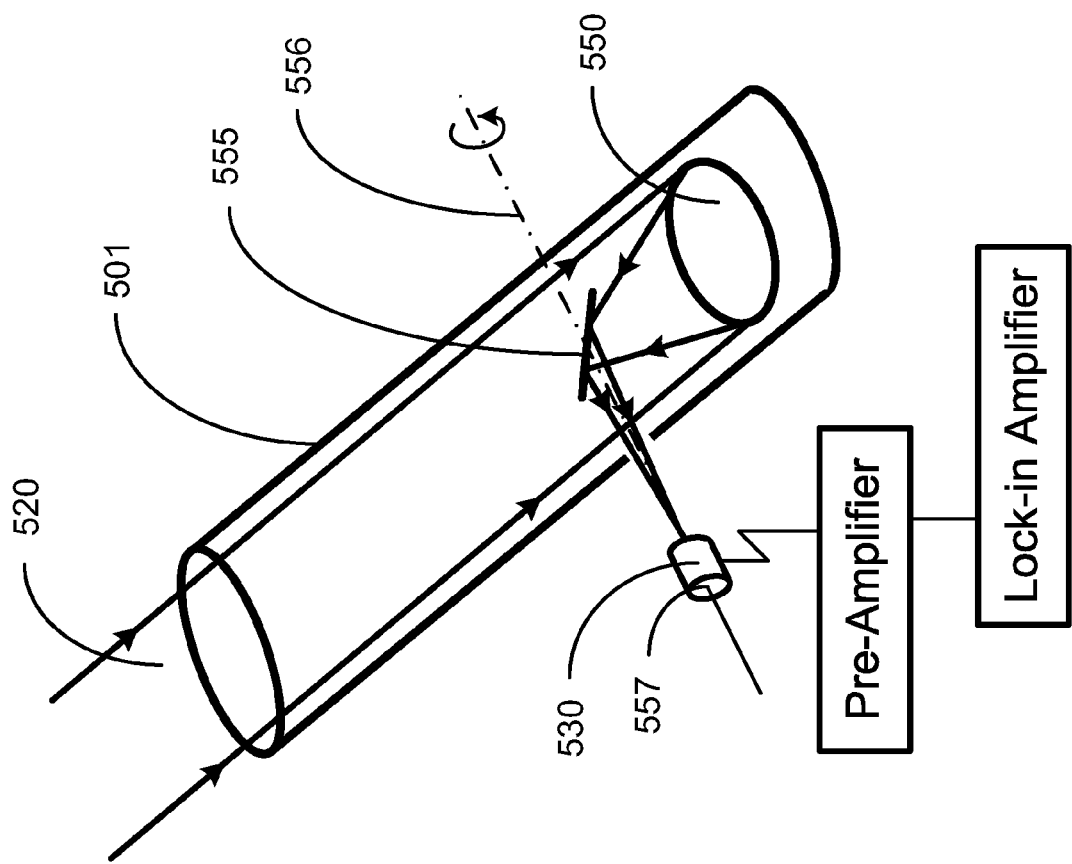
FIG. 5 shows schematically a collecting optics utilized in the remote sensing device according to one embodiment of the present invention.

According to the present invention, the detectors are positioned at the focus of the collecting optics. In one embodiment, the light collecting optics includes a Newtonian telescope, as shown in FIG. 5. The Newtonian telescope includes a single concave mirror 550 and a reflecting plate 555 placed inside a tube 501. The concave mirror 550 receives the beam of light 520 scattered from the surface of the lane of the road on which a vehicle is driven, and focuses it onto the plate 555. The plate 555 directs the light along its axis 556 to the focus 557 in which the detector 530 is placed. The focus 557 is outside the tube 501. The plate 555 is configured to rotate around the axis 556. The detector 530 is connected to a pre-amplifier and a lock-in amplifier.

Different sources need different detector systems. For a broadband light source, one or more filters are positioned in front of the detectors. Array detectors can be used to image strips of the road. This allows one to capture the entire exhaust plume and then to get absolute concentrations of the exhaust of a vehicle, irrelevant to the position or height of the tailpipe.

For an LED source, no filter is needed, although the LED source is a broadband source. An LED of different wavelengths has a different modulation frequency and therefore, each detector is connected to a separate lock-in amplifier.

Figure 6:
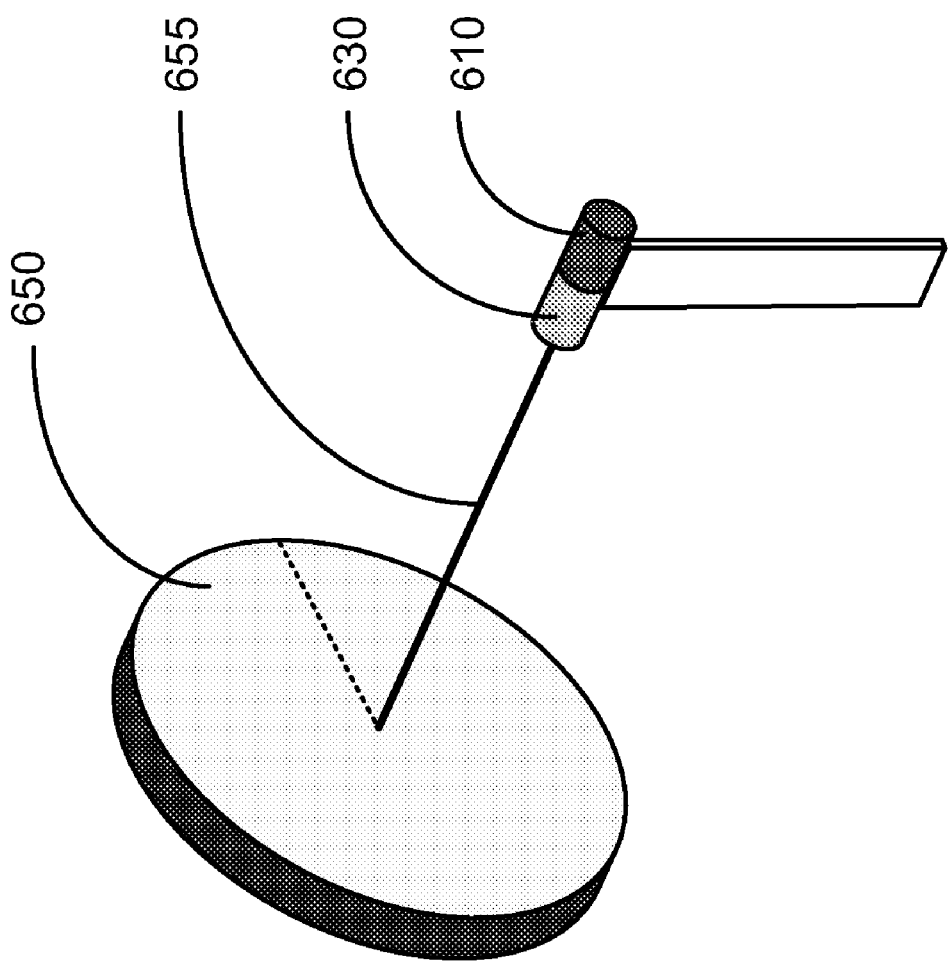
FIG. 6 shows schematically a collecting optics utilized in the remote sensing device according to another embodiment of the present invention.

For a diode laser source, the source 610 and the detector 630 are placed on the same optical axis 655, as shown in FIG. 6. The sphere mirror 650 serves as the collecting optics for collecting the scattered light scattered from the surface of the lane and focusing the collected light onto the detector 630. The laser source is brought into the mirror housing with optical fiber. The laser can be outside of the housing.

Figure 7:
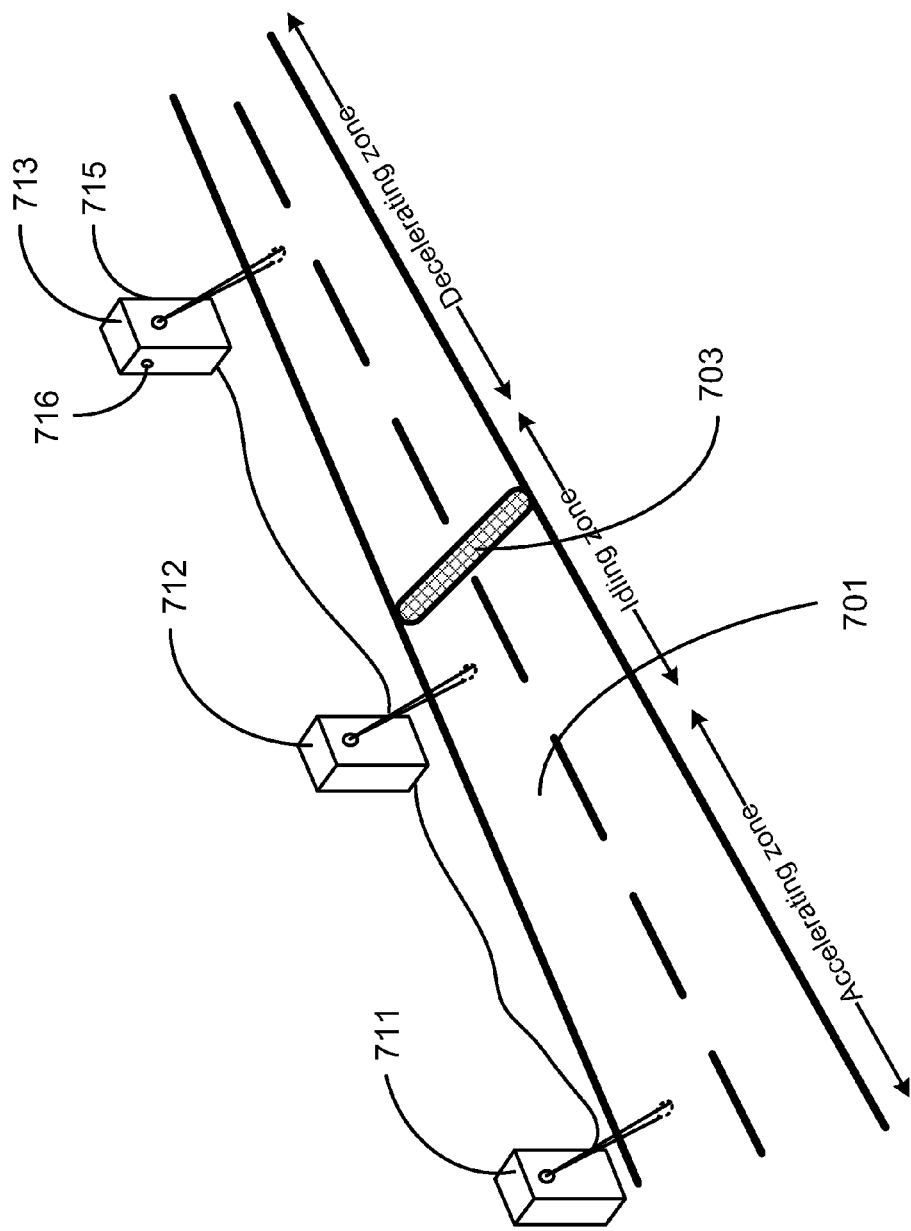
FIG. 7 shows schematically an application of the device of remote sensing of vehicle emission according to one embodiment of the present invention.

One of the main liabilities of remote sensing of car exhaust is that the mixing ratio changes depending on whether the vehicle/car is idling, accelerating or decelerating. In one embodiment, three remote sensing devices are used to detect the exhaust of the vehicle during idling, accelerating or decelerating. FIG. 7 shows schematically a setup of such a system in which one remote sensing device 711 is located in an accelerating zone, one 712 is located in an idling zone that is around the speed bump 703 placed on the road 701, and the other 713 is located in a decelerating zone. Additionally, a license recognition system 715 and a velocity radar system 716 are also incorporated into the remote sensing device 713. Accordingly, the measurements of the remote sensing devices 711, 712 and 713 are corresponding to the exhausts of a vehicle in the accelerating, idling and decelerating conditions, respectively.

In sum, the present invention, among other things, recites a remote sensing device that uses the LIDAR technology. The beam of light emitted from a source is directed downwards, transmitting through the exhaust plume, toward the surface of a traffic lane of a road on which the vehicle is driven. The transmitted light is then scattered at the surface of the traffic lane. A collecting optics is used to collect the scattered light from the surface of the traffic lane. The collected light is delivered to the detector for analyzing the components and concentrations of the exhaust plume. Additionally, according to the present invention, a detector array can be utilized to acquire images of the exhaust plume and the surface of the road, which would enable to unveil the whole picture of gas pollutants in the vehicle exhaust.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A device for remote sensing of emissions of a vehicle driven on a road, comprising:
   (a) a source for emitting a beam of light and transmitting the emitted light through an exhaust plume emitted from the vehicle to the surface of a lane of the road on which the vehicle is driven, wherein the transmitted light is scattered at the surface of the lane;
   (b) a detector for receiving at least one portion of the scattered light scattered from the surface of the lane; and
   (c) a processor for processing the received light therein to provide one or more spectra of the received light so as to determine components and concentrations of the exhaust plume,
   wherein the source and the detector are located in the same side of the road.

2. The device of claim 1, wherein the source comprises a halogen light source.

3. The device of claim 2, further comprising a collimating optics for collimating the emitted light and transmitting the collimated light through the exhaust plume to the surface of the lane.

4. The device of claim 3, wherein the collimating optics comprises a first concave mirror and a second concave mirror positioned in relation to the source such that the first concave mirror receives the beam of light emitted from the source and reflects the received light to the second concave mirror, the second concave mirror, in turn, collimates the reflected light and transmits the collimated light through the exhaust plume to the surface of the lane.

5. The device of claim 4, wherein the first concave mirror and the second concave mirror define a focus therebetween, and a chopper is placed on the focus.

6. The device of claim 2, further comprising one or more filters positioned in relation to the detector, each filter having a predetermined bandwidth.

7. The device of claim 1, wherein the source comprises light emitting diodes (LEDs).

8. The device of claim 1, wherein the source comprises a laser.

9. The device of claim 8, wherein the laser comprises a diode laser, and wherein both the source and the detector are placed on the same optical axis.

10. The device of claim 1, further comprising a collecting optics positioned in an optical path between the source and detector for collecting the scattered light scattered from the surface of the lane and delivering the collected light to the detector, wherein the collecting optics has a focus on the optical path, and wherein the detector is placed on the focus.

11. The device of claim 10, wherein the collecting optics comprises a Newtonian telescope.

12. The device of claim 10, wherein the collecting optics comprises a concave mirror.

13. The device of claim 1, wherein the detector comprises a plurality of photosensors, each photosensor generating an electrical signal responsive of the scattered light received, wherein the electrical signal is indicative of the absorption of the scattered light by the exhaust plume.

14. The device of claim 1, wherein the detector comprises a detector array capable of capturing images of the exhaust plume and the surface of the road.

15. The device of claim 1, wherein the processor comprises a spectrometer.

16. A device for remote sensing of emissions of a vehicle driven on a road, comprising:
   (a) a source for emitting a beam of light and transmitting the emitted light through an exhaust plume emitted from the vehicle to the surface of a lane of the road on which the vehicle is driven, wherein the transmitted light is scattered at the surface of the lane;
   (b) a detector for receiving light and processing the received light therein to provide one or more spectra of the received light, wherein the detector and the source are located in the same side of the road and define an optical path therebetween; and
   (c) a collecting optics positioned in the optical path for collecting the scattered light scattered from the surface of the lane and delivering the collected light to the detector.

17. The device of claim 16, wherein the source comprises a halogen light source, light emitting diodes (LEDs), or a laser.

18. The device of claim 16, wherein the collecting optics comprises a concave mirror or Newtonian telescope.

19. The device of claim 16, wherein the detector comprises a plurality of photosensors, each photosensor generating an electrical signal responsive of the scattered light received, wherein the electrical signal is indicative of the absorption of the scattered light by the exhaust plume.

20. The device of claim 19, wherein the detector further comprises a processor responsive to the electrical signals from the plurality of photosensors for determining components and concentrations of the exhaust plume.

21. The device of claim 16, wherein the detector comprises a detector array capable of capturing images of the exhaust plume and the surface of the road.

22. The device of claim 16, further comprising a license plate reader for identifying the vehicle to be detected.

23. The device of claim 22, further comprising a speed reader for detecting the speed of the vehicle so as to determine an exhaust pattern of the vehicle.

24. A device for remote sensing of emissions of a vehicle, comprising:
   (a) a source for emitting a beam of light and transmitting the emitted light through an exhaust plume emitted from the vehicle to a surface at which the transmitted light is scattered; and
   (b) a detector for receiving at least one portion of the scattered light scattered from the surface and processing the received light therein to provide one or more spectra of the received light so as to determine components and concentrations of the exhaust plume.

25. The device of claim 24, wherein the surface is corresponding to the bottom surface of a bridge through which the vehicle is driven.

26. The device of claim 24, wherein the surface is corresponding to the surface of a lane of a road on which the vehicle is driven.

* * * * *